United States Patent
Tanaka et al.

[11] Patent Number: 6,039,723
[45] Date of Patent: Mar. 21, 2000

[54] CATHETER

[75] Inventors: Junichi Tanaka, Angyouhara 930-32, Kawaguchi-shi, Saitama; Kunio Miyoshi, 10-18, Koushien 3-bancho, Nishinomita-shi, Hyougo; Sensuke Yamashita, 10-4, Kitarokkoudai 3-chome, Nishinomiya-shi, Hyougo, all of Japan

[73] Assignees: Junichi Tanaka, Kawaguchi; Kunio Miyoshi; Sensuke Yamashita, both of Nishinomiya, all of Japan

[21] Appl. No.: 08/969,014

[22] Filed: Nov. 12, 1997

[30] Foreign Application Priority Data

Nov. 12, 1996 [JP] Japan .................................. 8-300578
Oct. 14, 1997 [JP] Japan .................................. 9-280682

[51] Int. Cl.⁷ .................................................. A61M 25/00
[52] U.S. Cl. ............................................ 604/532; 604/523
[58] Field of Search ................................ 604/264, 280, 604/523, 530, 532

[56] References Cited

FOREIGN PATENT DOCUMENTS 3-198868  8/1991  Japan .
6-296695 10/1994  Japan .
7-308384 11/1995  Japan .

*Primary Examiner*—Corrine McDermott
*Attorney, Agent, or Firm*—Fish & Richardson P.C.

[57] ABSTRACT

A coronary artery angiographic and percutaneous transluminal coronary angioplasty guiding catheter includes a substantially tubular distal top portion having an open distal end, a substantially tubular proximal main portion, and a substantially tubular bend portion connectively provided between the distal top portion and the proximal main portion. An inclined portion is formed at the distal end of the distal top portion. The inclined portion is inclined such that a length of the distal top portion is shorter on an inside periphery of the bend portion than on an outside periphery of the bend portion. The inclined portion includes a closed portion being bent and sealed.

15 Claims, 9 Drawing Sheets

(1)

(2)

(3)

CATHETER

BACKGROUND OF THE INVENTION

The present invention relates to a catheter. More particularly, this invention relates to a coronary artery angiographic and percutaneous transluminal coronary angioplasty (hereinafter referred to as "PTCA") guiding catheter, a balloon catheter for percutaneous transluminal angioplasty, a balloon catheter for thrombus and embolus removal and a left coronary artery angiographic and PTCA guiding catheter.

Coronary artery angiography is conducted to examine the state of blood vessels of the heart. This coronary artery angiography is conducted by inserting various kinds of angiographic catheters into both the right coronary artery and the left coronary artery which derive from the aorta. Examples of such angiographic catheters are the Sones type which can be inserted into both the right coronary artery and the left coronary artery, and the Judkins type and the Amplatz type which each have two shapes for insertion into the right coronary artery and the left coronary artery.

An angiographic catheter which can be easily inserted into each of the right and left coronary arteries and which can be inserted, with one catheter, into both the right and left coronary arteries is disclosed in, for example, the Japanese Patent Laid-Open (Kokai) Publication No. HEI 3-198868 and in the Japanese Patent Laid-Open (Kokai) Publication No. HEI 7-308384.

On the other hand, there is a balloon catheter for thrombus removal, control of bleeding, angiography and arrest of bleeding during an operation, or expansion for arterial stenosis and opening and expansion for angiostenosis. This balloon catheter is inserted into, for example, a lumen of a guiding catheter and is guided to an object region.

However, during operation of the conventional catheter, may the end of the catheter collide with the inlet of a coronary artery or inner wall of a blood vessel. If there are repeated collisions in one region, that region may be injured or dissociated.

Accordingly, some ideas have been adopted such as construction of the end of the catheter with comparatively soft resins. However, the above-described problem has not been solved.

SUMMARY OF THE INVENTION

This invention aims at solving the above-described problem. It is an object of this invention to provide an angiographic and PTCA guiding catheter which can be easily inserted into the coronary arteries and which, upon the operation of the catheter, will not constitute a source of injury to the inlet of the coronary artery or inner walls of blood vessels by colliding with such regions.

In order to attain this object, this invention provides a coronary artery angiographic and PTCA guiding catheter, comprising: a top portion; a main portion; and a bend portion provided between the top portion and the main portion, and at the end of the top portion, an inclined portion is formed, being inclined in a manner such that the length of the top portion gradually becomes shorter from the side corresponding to the inside periphery of the bend portion toward the side corresponding to the outside periphery of the bend portion.

It is preferable that the coronary artery angiographic and PTCA guiding catheter of the above-described construction be used for a patient with the inlet of the coronary artery facing downward.

This invention also provides a coronary artery angiographic and PTCA guiding catheter, comprising: a top portion; a main portion; and a bend portion provided between the top portion and the main portion, and at the end of the top portion an inclined portion is formed, being inclined in a manner such that the length of the top portion gradually becomes longer from the side corresponding to the inside periphery of the bend portion toward the side corresponding to the outside periphery of the bend portion.

It is preferable that the coronary artery angiographic and PTCA guiding catheter of the above-described construction be used for a patient with the inlet of the coronary artery extending downward.

Moreover, this invention provides a balloon catheter for percutaneous transluminal angioplasty, which has at its end an inclined portion which is inclined gradually from one side to the other side.

Furthermore, this invention provides a balloon catheter for thrombus and embolus removal, which has at its end an inclined portion which is inclined gradually from one side to the other side.

Concerning the inclined portion, an angle of inclination on the side corresponding to the inside periphery of the bend portion may be set less than 90 degrees.

This construction makes it possible to extend the area of an end face of the catheter. Particularly, in the case of use for angiography, it is possible to provide a wide outlet for a contrast medium and to prevent the contrast medium from being injected against the inner wall of the coronary artery. Accordingly, it is possible to inject the contrast medium into a desirable region with more certainty and efficiency.

If the angle of inclination is set at 30 degrees or more and less than 90 degrees, the above-described advantage will increase even more.

It is possible to fabricate the top side of the inclined portion of a closed portion such that it is bent and closed. This construction makes it possible to further prevent, upon the operation of the catheter, the top of the inclined portion from colliding with the inlet of the coronary artery or the inner walls of the blood vessels so that such regions will not be injured or dissociated.

Concerning the closed portion, the radius of curvature of the outside periphery can be set within the range of 0.1 mm to 5.0 mm.

It is also possible to form, at the end of the top portion and continuous to the closed portion, a fourth bend portion and a fifth bend portion in the order closer to the closed portion. The fourth bend portion can be bent with the radius of curvature of the outside periphery ranging from 0.5 mm to 5.0 mm. The fifth bend portion can be bent with the radius of curvature of the outside periphery ranging from 0.5 mm to 10.0 mm.

Moreover, this invention provides a coronary artery angiographic and PTCA guiding catheter, comprising: a top portion; a main portion; and a bend portion provided between the top portion and the main portion, and the end of the top portion is composed of a closed sphere and an opening is formed at a position close to the sphere of the top portion.

This construction makes it possible to further prevent, upon the operation of the catheter, the top of the inclined portion from colliding with the inlet of the coronary artery or the inner walls of the blood vessels so that such regions will not be injured or dissociated.

An opening area of the opening can be made 1.0 to 2.0 times as large as a cross-sectional area of the top portion as cut in a direction perpendicular to the lengthwise direction of the top portion.

The radius of curvature of the sphere can be set exceeding one half of the outside diameter of the catheter and not more than the outside diameter of the catheter.

Moreover, the opening can be formed from a position 1.0 mm to 10.0 mm apart from the top of the sphere toward the base end side of the catheter.

Furthermore, it is possible to form a sphere inside the end of the top portion, the sphere having a larger radius of curvature than that of the sphere described above.

This invention also provides a coronary artery angiographic and PTCA guiding catheter, comprising: a top portion; a main portion; and a bend portion provided between the top portion and the main portion, and the end of the top portion is formed to gradually widen toward the outside and is constructed in a manner such that a cross-sectional area of this portion as cut in a direction perpendicular to the lengthwise direction gradually increases toward the end.

This construction makes it possible to extend the area of an end face of the catheter. Particularly, in the case of use for angiography, it is possible to provide a wide outlet for a contrast medium and to prevent the contrast medium from being injected against the inner wall of the coronary artery. Accordingly, it is possible to inject the contrast medium into a desirable region with more certainty and efficiency. If the top portion of the catheter is formed with a soft material, when the top portion collides with the inner walls of the coronary artery or blood vessels, the top portion may be sometimes crushed inwardly and the outlet (or opening or lumen) for the contrast medium will become narrow. However, if the above-described construction of the catheter with a wide end face is applied, such a problem will be solved.

The end of the top portion can be bent outward with the radius of curvature ranging from 1.0 mm to 100.0 mm.

This invention also provides a left coronary artery angiographic and PTCA guiding catheter, comprising: a top portion; a main portion; and a bend portion provided between the top portion and the main portion. The bend portion comprises: a first bend portion formed closer to the main portion and having a radius of curvature of the outside periphery within the range of 5.0 mm to 15.0 mm; a second bend portion formed closer to the top portion and being bent in the same direction as that of the first bend portion and having a radius of curvature of the outside periphery within the range of 3.0 mm to 9.0 mm; a first straight portion provided between the first bend portion and the second bend portion and at an angle with the main portion ranging from more than 0 degrees to not more than 45 degrees; and a second straight portion provided between the second bend portion and the top portion and at an angle with the main portion ranging from not less than 10 degrees to not more than 135 degrees, and the top portion comprises a third bend portion being bent in a direction opposite to that of the bend portion and having a radius of curvature of the outside periphery within the range of 3.0 mm to 9.0 mm.

The catheter of this construction can be easily inserted into the coronary artery and, upon the operation of the catheter, the end of the catheter will be restrained from colliding with the inner walls of the left coronary artery or blood vessels so that such regions will not be injured or dissociated.

If the radius of curvature of the outside periphery of the first bend portion is less than 5.0 mm or more than 15.0 mm, it will become difficult to obtain the above-described advantage.

If the radius of curvature of the outside periphery of the second bend portion is less than 3.0 mm or more than 9.0 mm, it will become difficult to obtain the above-described advantage.

If the angle formed by the first straight portion and the main portion exceeds 45 degrees, it will become difficult to obtain the above-described advantage.

If the angle formed by the second straight portion and the main portion is less than 10 degrees or more than 135 degrees, it will become difficult to obtain the above-described advantage.

If the radius of curvature of the outside periphery of the third bend portion is less than 3.0 mm or more than 9.0 mm, it will become difficult to obtain the above-described advantage.

The top portion can be provided with, at the end of the third bend portion, a third straight portion at an angle with the main portion being more than 0 degrees and not more than 85 degrees. If the angle formed by the third straight portion and the main portion is more than 85 degrees, it will become difficult to obtain the above-described advantage.

Moreover, the end of the top portion can be formed closer to the main portion than from the second bend portion.

Furthermore, a distance X between a line $L_1$, which is a tangent of the first bend portion and perpendicularly intersects the main portion, and a line $L_2$, which passes the end of the top portion and perpendicularly intersects the main portion, can be set within the range of 34.0 mm to 55.0 mm.

A ratio (X:Y) of the distance X to a distance Y between a line $L_3$, which passes a boundary point of the bend portion and the top portion and perpendicularly intersects the main portion, and the line $L_2$ can be set within the range of 34.0 mm:1.0 mm to 55.0 mm:5.0 mm.

The outside diameter can be set within the range of 3 French to 10 French. The term "French (or Fr)" herein used shall mean a unit indicating the outside diameter of a catheter and 3 Fr can be converted into 1.0 mm.

This invention also provides a catheter constructed in a manner such that the end of a top portion gradually widens toward the outside and that a cross-sectional area of the end of the top portion as cut in a direction perpendicular to the lengthwise direction gradually increases toward the end.

The end of the top portion can be bent outward with the radius of curvature ranging from 1.0 mm to 100.0 mm.

Moreover, this invention provides a catheter having an inclined portion formed at the end of its top portion, the inclined portion being inclined in a manner such that the length of the top portion gradually decreases from one side toward the other side, and the top side of the inclined portion comprising a closed portion being bent and closed.

Furthermore, this invention provides a catheter comprising a sphere formed by closing the end of a top portion and having an opening formed close to the sphere of the top portion.

DETAILED DESCRIPTION OF THE INVENTION

Embodiments of this invention are hereinafter explained by referring to drawings.

Embodiment 1

Figure 1:
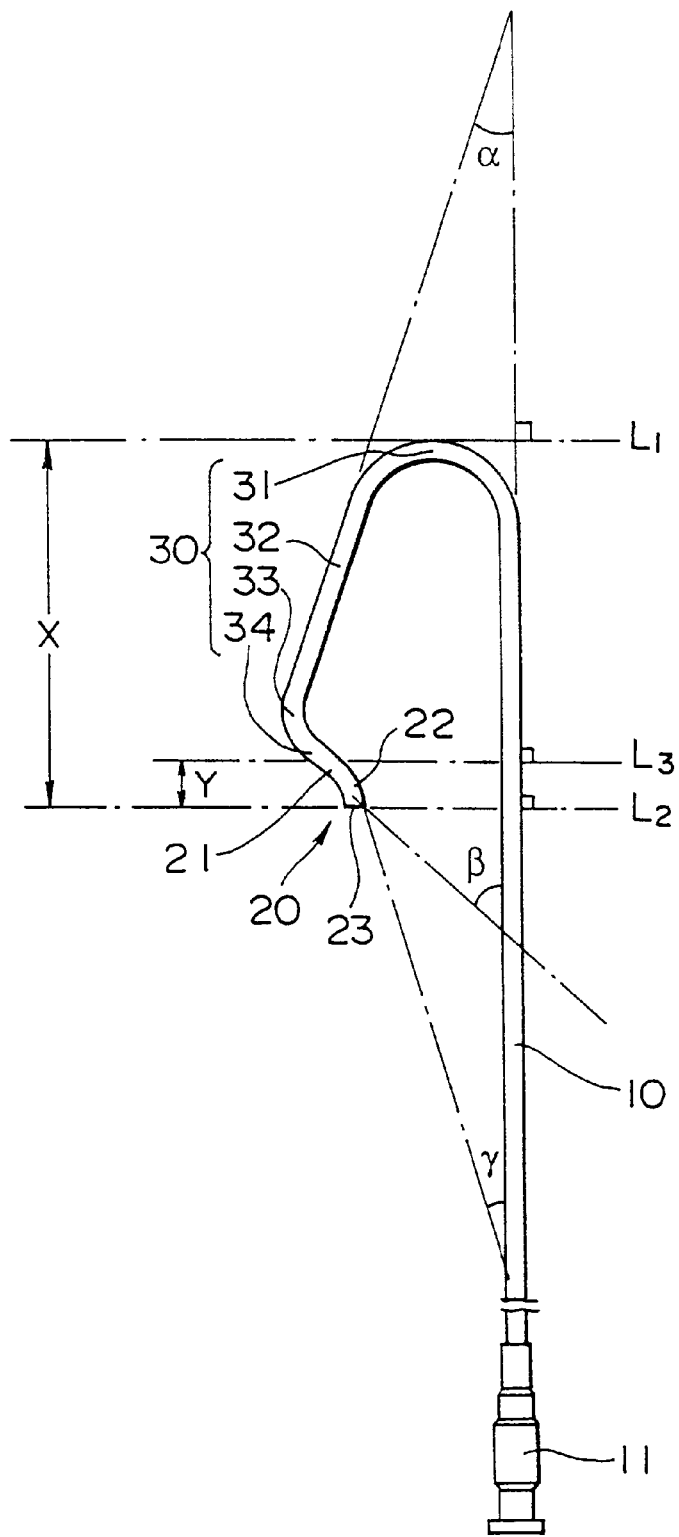
FIG. 1 is a plan view of an angiographic catheter according to Embodiment 1 of this invention.

FIG. 1 is a plan view of an angiographic catheter according to Embodiment 1 of this invention. In Embodiment 1, an angiographic catheter with a 5 Fr outside diameter is used as an example for explanation.

An angiographic catheter 1 shown in FIG. 1 used for angiography of the left coronary artery and is composed of a main portion 10, a top portion 20, a bend portion 30 provided between the main portion 10 and the top portion 20, and a hub 11 mounted on a base end of the main portion 10.

The bend portion 30 is composed of, in the order closer to the main portion 10, a first bend portion 31 formed continuous to the end of the main portion 10, a first straight portion 32 formed continuous to the first bend portion 31, a second bend portion 33 formed continuously to the first straight portion 32, and a second straight portion 34 formed continuous to the second bend portion 33.

The first bend portion 31 comprises a bend with a 10.0 mm radius of curvature of the outside periphery. Concerning this first bend portion 31, the length of a circular arc of the bend is set in a manner such that an angle α formed by the first straight line 32 and the main portion 10 becomes 20 degrees. The second bend portion 33 is bent in the same direction as that of the first bend portion 31 and comprises a bend with a 6.0 mm radius of curvature of the outside periphery. Concerning this second bend portion 33, the length of a circular arc of the bend is set in a manner such that an angle β formed by the second straight line 34 and the main portion 10 becomes 55 degrees.

The top portion 20 is formed continuous to at the end of the bend portion 30 and is composed of a third bend portion 21, which is bent in a direction opposite to that of the bend portion 30, and a third straight portion 22 which is formed continuous to the third bend portion 21.

The third bend portion 21 comprises a bend with a 6.0 mm radius of curvature of the outside periphery. Concerning this third bend portion 21, the length of a circular arc of the bend is set in a manner such that an angle γ formed by the third straight line 22 and the main portion 10 becomes 20 degrees. The end 23 of the top portion 20 is located closer to the main portion 10 than from the second bend portion 33.

Embodiment 1 is designed in a manner such that a distance X between a line $L_1$, which is a tangent of the first bend portion 31 and perpendicularly intersects the main portion 10, and a line $L_2$, which passes the end 23 of the top portion 20 and perpendicularly intersects the main portion 10, becomes 40.0 mm. Moreover, it is designed in a manner such that a ratio (X:Y) of the distance X to a distance Y between a line $L_3$, which passes a boundary point of the bend portion 30 and the top portion 20 and perpendicularly intersects the main portion 10, and the line $L_2$ becomes 40.0 mm:3.0 mm.

It is preferable that a distance between a central point (or vertex) of the second bend portion 33 and a central point (or vertex) of the third bend portion 21 be set within the range of 5.0 mm to 20.0 mm.

Concerning the angiographic catheter 1 of Embodiment 1, it is possible to select and use appropriate materials among, for example, polyethylene resins, fluorocarbon resins, polyether polyurethane resins, polyester polyurethane resins, polyamide resins, polyester polyamide resins, and polyether polyamide resins. Constituent materials for the inside (or inside layer) or the outside (or outside layer) of the angiographic catheter 1 may be the same or different. It is specifically preferable that polyamide resins, polyester polyamide resins and polyether polyamide resins be used because these resins have a high shape memory and are capable of providing toughness which is essentially required for a catheter.

The angiographic catheter 1 according to Embodiment 1 can use the same cross-sectional construction and basic functions as those of a conventional angiographic catheter. This will never cause its essential functions as a catheter to be impaired.

Specific movements of the angiographic catheter 1 of this construction are hereinafter explained with reference to FIG. 2.

Figure 2:
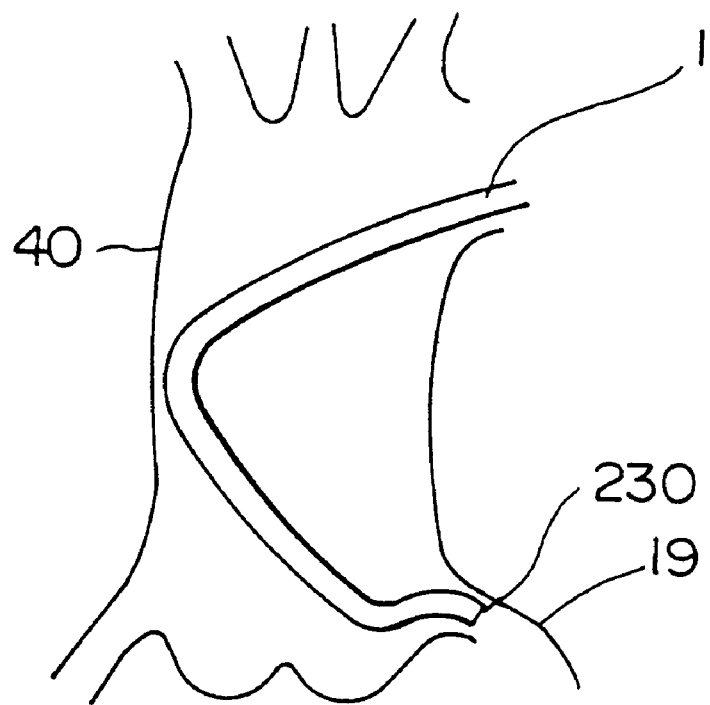
FIG. 2 is a model view of the angiographic catheter according to Embodiment 1 being inserted and placed in the left coronary artery.

FIG. 2 is a model view of the angiographic catheter 1 according to Embodiment 1 which is inserted and replaced in the left coronary artery.

First, as in a normal procedure the end 23 of the catheter 1 is moved forward until its in an ascending aorta of the aorta 40. Specifically speaking, by applying, for example, the Seldinger Technique, a catheter introducer is inserted into the femoral artery, the catheter 1 with a guide wire pierced through at a predetermined position thereof is then inserted into a sheath of the catheter introducer, and the guide wire is moved ahead of the catheter 1 and the end 23 of the catheter 1 is introduced through a top hole of the sheath into the femoral artery. Subsequently, the catheter 1 is gradually delivered and inserted into the femoral artery. At such time, because the end 23 of the catheter 1 passes bends of blood vessels or in order to select branches of blood vessels, the operation is conducted by combining the following actions as appropriate: pushing forth or pulling back the guide wire; moving the catheter 1 back and forth; and turning the catheter 1.

When the end 23 of the catheter 1 has reached the starting point of the aorta, the guide wire is pulled out and the operation is conducted so that the end 23 of the catheter 1 will reach the left coronary arterial without any object in the inner lumen of end 23. During this operation, since the catheter 1 has the aforementioned construction, it is possible to prevent the end 23 from colliding with the inlet of the left coronary artery or to prevent, for example, inner walls of blood vessels from being injured. Accordingly, it is possible to restrain the catheter 1 from injuring or dissociating such regions during the operation of the catheter 1.

Next, a test angiography injection is conducted in order to confirm placement of end 23 in an inlet position of the left coronary artery. If the inlet position of the left coronary artery is confirmed, the catheter 1 is moved and the end 23 is slowly inserted into the left coronary artery 19.

Subsequently, while a patient is instructed to breathe deeply, the catheter 1 is moved forward a short distance and the end 23 is then inserted into the left main coronary artery.

After the end 23 of the catheter 1 is inserted into the left coronary artery 19 by conducting the above-described operation, a connector is connected to the base of the lumen and a contrast medium is injected.

According to Embodiment 1, the radius of curvature of the outside periphery concerning the first bend portion 31 is set as 10.0 mm. However, without limitation to this value, the radius of curvature of the outside periphery of the first bend portion 31 may be set within the range of 5.0 mm to 15.0 mm.

Concerning the first bend portion 31, the length of the circular arc of the bend is set in a manner such that the angle formed by the first straight line 32 and the main portion 10 becomes 20 degrees. However, without limitation to this value, the length of the circular arc of the first bend portion 31 may be set in a manner such that the angle α formed by the first straight line 32 and the main portion 10 is more than 0 degrees and not more than 135 degrees.

According to Embodiment 1, the radius of curvature of the outside periphery of the second bend portion 33 is set as 6.0 mm. However, without limitation to this value, the radius of curvature of the outside periphery of the second bend portion 33 may be set within the range of 3.0 mm to 9.0 mm.

Concerning the second bend portion 33, the length of the circular arc of the bend is set in a manner such that the angle formed by the second straight line 34 and the main portion 10 is 55 degrees. However, without limitation to this value, the length of the circular arc of the second bend portion 33 may be set in a manner such that the angle β formed by the second straight line 34 and the main portion 10 is within the range of 10 degrees to 135 degrees.

According to Embodiment 1, the radius of curvature of the outside periphery of the third bend portion 21 is set as 6.0 mm. However, without limitation to this value, the radius of curvature of the outside periphery of the third bend portion 21 may be set within the value of 3.0 mm to 9.0 mm.

Concerning the third bend portion 21, the length of the circular arc of the bend is set in a manner such that the angle formed by the third straight line 22 and the main portion 10 is 20 degrees. However, without limitation to this value, the length of the circular arc of the third bend portion 21 may be set in a manner such that the angle γ formed by the third straight line 22 and the main portion 10 is more than 0 degrees and not more than 85 degrees.

Moreover, according to Embodiment 1, the top portion 20 is composed of the third bend portion 21 and the third straight portion 22. However, without limitation to this construction, the top portion 20 may be composed of only the third bend portion 21. In this case, the length of the circular arc of the third bend portion 21 may be adjusted optionally.

Furthermore, according to Embodiment 1, the distance X is set as 40.0 mm. However, without limitation to this value, it is preferable that the distance X be set within the range of 34.0 mm to 55.0 mm. Also, the ratio of the distance X to the distance Y is set as 40.0 mm:3.0 mm. However, it is preferable that the ratio of the distance X to the distance Y be set within the range of 34.0 mm:1.0 mm to 55.0 mm:5.0 mm.

Concerning Embodiment 1, an explanation has been given about the method of inserting the catheter 1 from the femoral artery. However, without limitation to this method, it is possible to insert the catheter of this invention from a brachial artery. In this case, the outside diameter of the catheter 1 may be decided optionally.

Moreover, the end of the angiographic catheter according to Embodiment 1 may be composed of, for example, comparatively soft resins.

Embodiment 2

Concerning Embodiment 2, an explanation is given about a guiding catheter used to guide a balloon catheter for endermic percutaneous transluminal angioplasty, which opens and expands a blood vessel of angiostenosis, to the left coronary artery. With Embodiment 2, a guiding catheter with an 8 Fr outside diameter is used as an example for explanation. The same reference numerals as used in Embodiment 1 of catheter 1 is given to an element of the same shape (however, with a different outside diameter) in Embodiment 2. Any detailed descriptions about such elements are omitted, and detailed descriptions about the same operation as described in Embodiment 1 are omitted.

The appearance of the guiding catheter of Embodiment 2 is the same as that of the catheter 1 of Embodiment 1, except that the guiding catheter of Embodiment 2 has a larger outside diameter. The cross-sectional construction and basic functions, etc. of the guiding catheter of Embodiment 2 are the same as those of conventional catheters.

Specific movements of this guiding catheter 2 are hereinafter explained with reference to drawings.

Figure 3:
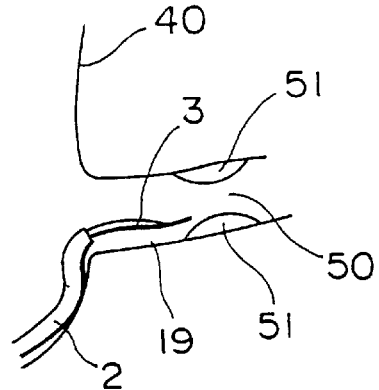
FIG. 3 shows model views of the left coronary artery for which a stenosis treatment is conducted by using a balloon catheter for endermic percutaneous transluminal angioplasty by means of a guiding catheter according to Embodiment 2.
Figure 3:
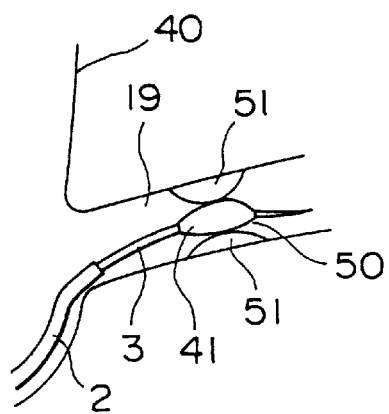
Figure 3:
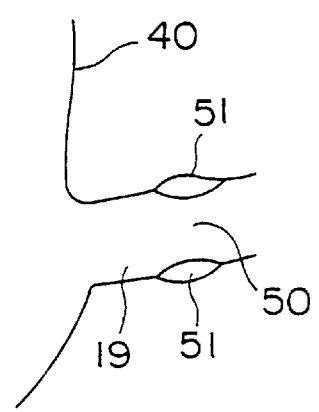

FIG. 3 shows model views of the left coronary artery for which a stenosis treatment is conducted by using a balloon catheter 3 for endermic percutaneous transluminal angioplasty by means of the guiding catheter 2 according to Embodiment 2. These are enlarged views of a region around the left coronary artery as shown in FIG. 2.

First, the guiding catheter 2 is operated by the same method as that of Embodiment 1 so that the end 23 of the guiding catheter 2 will reach the left coronary arterial without any object in the inner lumen of end 23. However, with Embodiment 2, the catheter 2 is inserted from the femoral artery. At this operation, just as in the case of Embodiment 1, it is possible to prevent the end 23 of the catheter 2 from colliding with valves of the heart or inner walls of blood vessels during the operation of the catheter 2.

At the step shown in FIG. 3(1), the guiding catheter 2 is moved to slowly insert the end 23 into the left coronary artery 19 until in a desirable position.

At the step shown in FIG. 3(2), the balloon catheter 3 is inserted into the guiding catheter 2 and a balloon 41 is moved forward until at a stenosis region 50 where thrombi 51 are formed. Subsequently, a contrast medium which is about 50% diluted with a physiological salt solution is injected into the balloon 41 to make the balloon 41 expand, thereby expanding the stenosis region 50.

As shown in FIG. 3(3), through the above-described operation, the stenosis treatment has been conducted by pushing the thrombi 51 toward the outside of the left coronary artery and thereby expanding the stenosis region.

As described above, it is possible to use the catheter of this invention both for the left coronary artery angiography and for the guiding purpose by optionally selecting the outside diameter.

Embodiment 3

Concerning Embodiment 3, an explanation is hereinafter given about the case where an inclined portion is provided at the end of the top portion of the angiographic catheter. Embodiment 3 shows an example in which the catheter is used for a patient with the inlet of the left coronary artery extending downward.

Figure 4:
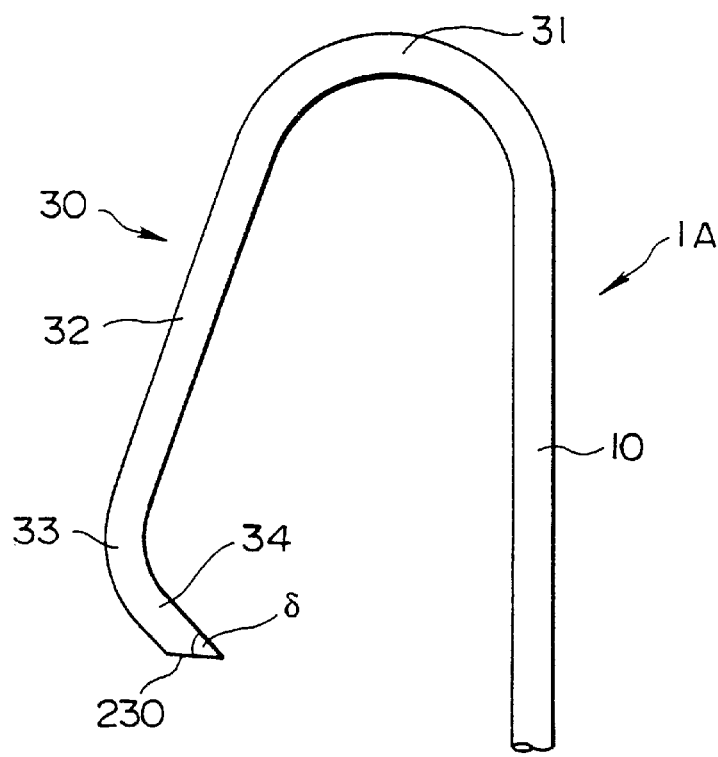
FIG. 4 is a plan view of a top portion of an angiographic catheter according to Embodiment 3.

FIG. 4 is a plan view of the top portion of the angiographic catheter according to Embodiment 3. The same reference numerals used in the angiographic catheter of Embodiment 1 are used with each element of the same construction as of Embodiment 3. Any detailed descriptions about such elements are omitted.

Concerning an angiographic catheter 1A shown in FIG. 4, an inclined portion 230 is formed at the end of the second straight portion 34. Namely, the angiographic catheter 1A is constructed in a manner such that the inclined portion 230 is formed instead of providing the third bend portion 21 and the third straight portion 22.

This inclined portion 230 is formed to be inclined in a manner such that the length of the second straight portion gradually becomes shorter from the side corresponding to the inside periphery of the bend portion 30 to the side corresponding to the outside periphery of the bend portion 30. The inclined portion 230 is designed so that the angle of inclinations on the side corresponding to the inside periphery of the bend portion is 60 degrees.

Figure 5:
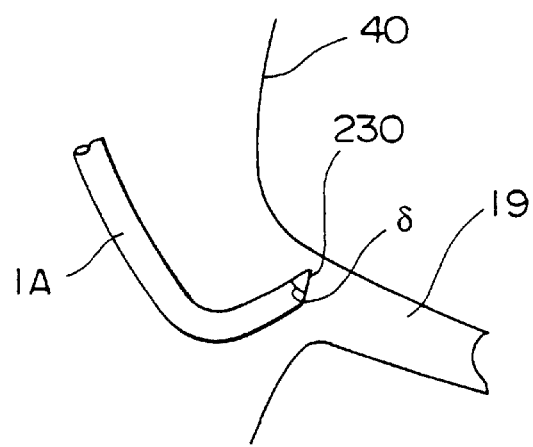
FIG. 5 is a model view of the top portion of the angiographic catheter according to Embodiment 3 being inserted and placed in the left coronary artery.

FIG. 5 is a model view of the angiographic catheter 1A according to Embodiment 3 being inserted and placed in the left coronary artery.

As is apparent from FIGS. 4 and 5, in comparison with the angiographic catheter 1 (of the construction with no inclined portion formed at the end 23 of the top portion 20) as explained in Embodiment 1, the angiographic catheter 1A of this construction can have a wider outlet for a contrast medium and it is possible to prevent the contrast medium from being injected into the inner walls of the left coronary artery. Accordingly, it is possible to inject the contrast medium into a desirable region with more certainty and efficiency.

Concerning Embodiment 3, an explanation has been given about the case in which the inclined portion 230 is provided at the end of the second straight line 34 of the angiographic catheter of Embodiment 1. However, without limitation to this construction, the inclined portion 230 may be provided, for example, at the end of the third bend portion 21 of the angiographic catheter of Embodiment 1. In this case, however, it is preferable to set the length of the third bend portion 21 (length from a boundary position between the second straight portion 34 and the third bend portion 21 to the end of the third bend portion 21) as 5.0 mm or shorter.

Concerning Embodiment 3, an explanation has been given about the case in which the inclined portion 230 is formed on the left coronary artery angiographic and PTCA guiding catheter. However, without limitation to this construction, the same effect can be obtained when the inclined portion 230 is provided at the end of a left coronary artery angiographic and PTCA guiding catheter of other constructions, provided that such a catheter should comprise a top portion, a main portion, and a bend portion provided between the top portion and the main portion.

Figure 6:
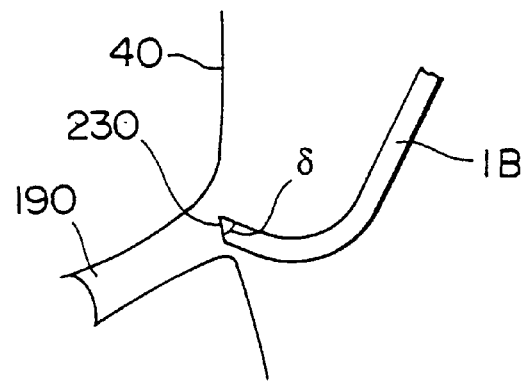
FIG. 6 is a model view of the top portion of the angiographic catheter according to another embodiment of this invention being inserted and placed in the right coronary artery.

Moreover, other than the left coronary artery angiographic and PTCA guiding catheter, the inclined portion 230 may be formed on a right coronary artery angiographic and PTCA guiding catheter (see FIG. 6), a balloon catheter for percutaneous transluminal angioplasty or a balloon catheter for thrombus and embolus removal. In FIG. 6, a reference numeral 1B indicates an angiographic catheter and a reference numeral 190 indicates the right coronary artery.

Figure 7:
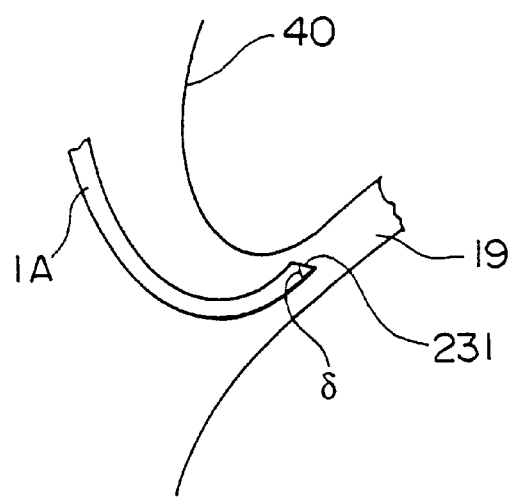
FIG. 7 is a model view of the top portion of the angiographic catheter according to another embodiment of this invention being inserted and placed in the left coronary artery with its inlet extending-upward.

Concerning Embodiment 3, the example is shown in which the catheter is used for a patient with the inlet of the left coronary artery extending downward. However, referring to FIG. 7, without limitation to such usage, the catheter of Embodiment 3 may be used for a patient with the inlet of the coronary artery extending upward by forming an inclined portion 231 which is inclined in a direction opposite to that of the inclined portion 230.

Concerning Embodiment 3, the angle of inclination δ of the inclined portion 230 is set as 60 degrees. However, without limitation to this value, it is preferable to set the angle of inclination δ as less than 90 degrees, more preferably, 30 degrees or more and less than 90 degrees.

Moreover, the end of the angiographic catheter of Embodiment 3, including the inclined portion 230, may be composed of, for example, comparatively soft resins.

Needless to say, the end of the inclined portion on the side corresponding to the inside periphery of the bend portion may be made in a round shape which is moderately rounded.

Embodiment 4

Concerning Embodiment 4, an explanation is hereinafter given about the case where a closed portion is provided on the top side of the inclined portion which is formed at the end of the angiographic catheter as explained in Embodiment 3.

Figure 8:
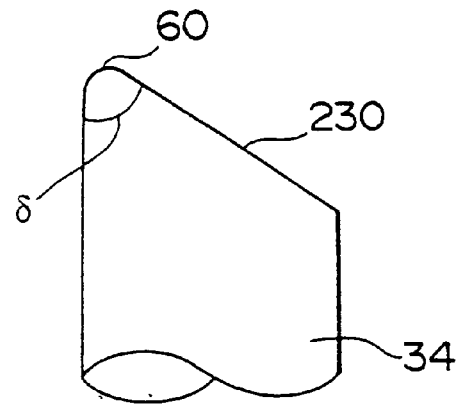
FIG. 8 is an enlarged plan view of the top portion of an angiographic catheter according to Embodiment 4 of this invention.

FIG. 8 is an enlarged plan view of the top portion of the angiographic catheter according to Embodiment 4. The same reference numeral used for the angiographic catheter explained in Embodiments 1 and 3 are given to each element of the same construction in Embodiment 4. Any detailed descriptions about such elements are omitted.

With the angiographic catheter shown in FIG. 8, a closed portion 60 which is bent and closed is formed on the top side of the inclined portion 230 formed at the end of the top portion 34. A radius of curvature of this closed portion is set as 0.6 mm.

As mentioned above, since the top side of the inclined portion 230 becomes the closed portion 60, if upon the operation of the angiographic catheter the closed portion 60 which is the end of the inclined portion 230 contacts, for example, the inlet of a coronary artery or the inner walls of blood vessels, it is possible to sufficiently prevent such touched regions from being injured or dissociated.

Concerning Embodiment 4, an explanation has been given about the case in which the closed portion 60 is formed on the top side of the inclined portion 230 with the angle of inclination δ being 60 degrees. However, without limitation to this value, the angle of inclination δ of the inclined portion 230 may be less than 90 degrees.

Figure 9:
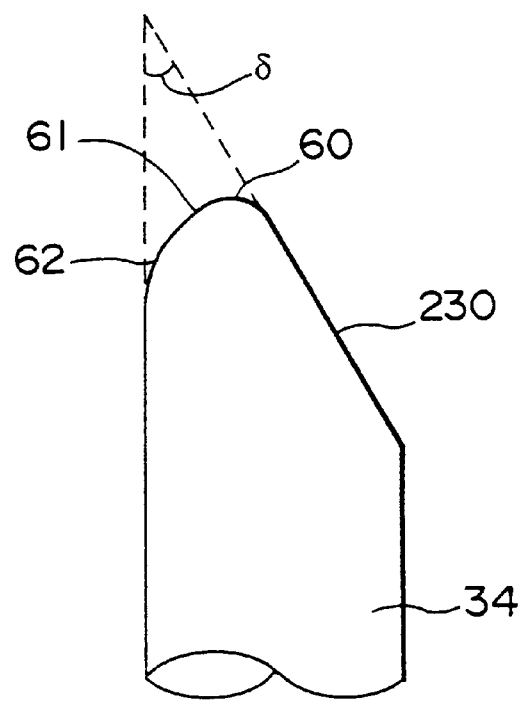
FIG. 9 is an enlarged plan view of the top portion of the angiographic catheter according to another embodiment of this invention.

According to this invention, as shown in FIG. 9, it is also possible to form a fourth bend portion 61 and a fifth bend portion 62, in the order closer to the closed portion 60, at the end of the top portion 34 and continuous to the closed portion 60. In FIG. 9, the angle of inclination δ is 30 degrees.

According to the embodiment shown in FIG. 9, the radius of curvature of the fourth bend portion 61 is set as 0.6 mm and the radius of curvature off the fifth bend portion 62 is set as 0.8 mm.

Figure 10:
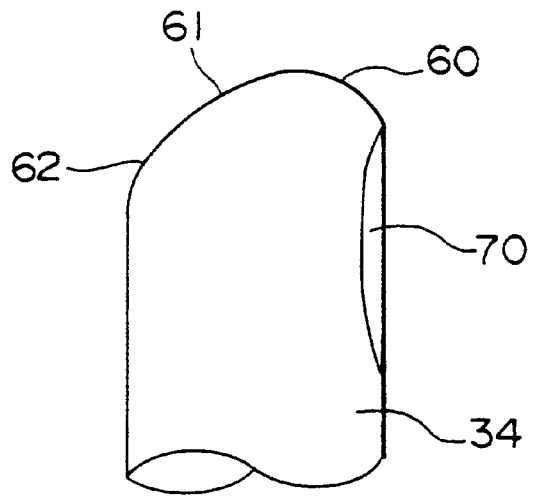
FIG. 10 is an enlarged plan view of the top portion of the angiographic catheter according to another embodiment of this invention.

Moreover, according to this invention, as shown in FIG. 10, the closed portion 60, the fourth bend portion 61 and the fifth bend portion 62 may be formed at the endmost position of the top portion 34. In other words, the angle of inclination may be set as 0 degrees (or 180 degrees). Moreover, an opening (or lumen) 70 may be formed on the wall of the top portion 34 and near the closed portion 60. In this case, it is preferable that an opening area of the opening 70 be set as 1.0 to 2.0 times as large as a cross-sectional area of the top portion 34 as cut in a direction perpendicular to the lengthwise direction.

According to the embodiment shown in FIG. 10, the radius of curvature of the fourth bend portion 61 is set as 0.6 mm and the radius of curvature of the fifth bend portion 62 is set as 0.8 mm.

Concerning Embodiment 4, an explanation has been given bout the case where the radius of curvature of the closed portion 60 is 0.6 mm. However, without limitation to this value, it is referable that the radius of curvature of the closed portion 60 be within the range of 0.1 mm to 5.0 mm.

Furthermore, it is preferable that the radius of curvature of the fourth bend portion 61 be within the range of 0.5 mm to 5.0 mm and the radius of curvature of the fifth bend portion 62 be within the range of 0.5 mm to 10.0 mm.

Needless to say, it is possible to apply the closed portion 60, the fourth bend portion 61 and the fifth bend portion 62 as explained in Embodiment 4 to the catheter as explained in Embodiment 2 or any catheters of other constructions.

Embodiment 5

Embodiment 5 of this invention is hereinafter explained with reference to a drawing. Concerning Embodiment 5, an explanation is given about a mode in which the end shape of the angiographic catheter as explained in Embodiment 3 is changed.

Figure 11:
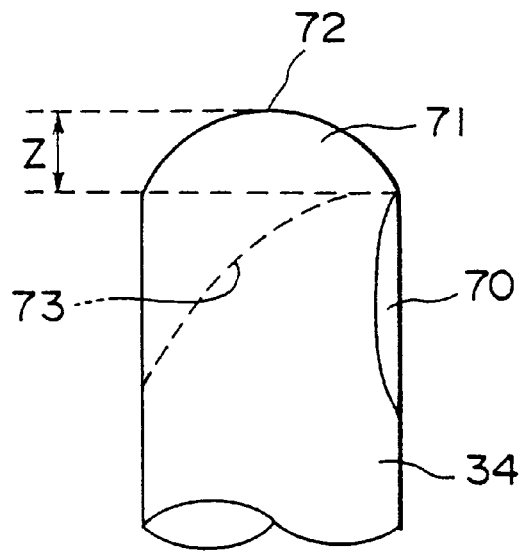
FIG. 11 is an enlarged plan view of the top portion of an angiographic catheter according to Embodiment 5 of this invention.

FIG. 11 is an enlarged plan view of the top portion of the angiographic catheter according to Embodiment 5. The same reference numerals as used in the preceding embodiments of the angiographic catheter are given to each element of the same construction in Embodiment 5. Any detailed descriptions about such elements are omitted.

Concerning the angiographic catheter shown in FIG. 11, a closed sphere 71 is formed at the endmost position of the top portion 34. A center 72 of the sphere 71 is located along the center line extending in the lengthwise direction of the top portion 34. The radius of curvature of the sphere 71 is set as 0.84 mm.

An opening (or lumen) 70 is formed at a position close to the base end side of the sphere 71 of the top portion 34. This opening 71 opens from a position 0.56 mm apart from the center 72 (or vertex) of the sphere 71 toward the base end side. Namely, the distance indicated with the letter Z in FIG. 11 is 0.56 mm.

A gentle sphere 73 which starts from near the edge of the opening 70 is formed inside the end of the top portion 34. The radius of curvature of this sphere 73 is set as 1.70 mm. This means that the angiographic catheter as shown in FIG. 11 is constructed in a manner such that a thickness (or wall thickness) of the end of the top portion becomes thick. Accordingly, even if the end of the angiographic catheter touches, for example, inner walls of the left coronary artery or blood vessels, it is possible to prevent the opening 70 from being crushed, thereby being capable of securing the outlet for a contrast medium and injecting the contrast medium efficiently.

Since the end of the catheter is spherical shaped even if the end of the catheter contacts, for example, inner walls of a coronary artery or blood vessel, it is possible to restrain such contacted regions from being injured or dissociated. The end of the catheter may be composed of, for example, soft resins.

Concerning Embodiment 5 as well, it is preferable that the opening area of the opening 70 be set as 1.0 to 2.0 times as large as the cross-sectional area of the top portion 34 as cut in a direction perpendicular to the lengthwise direction.

Concerning Embodiment 5, an explanation has been given about the case where the radius of curvature is set as 0.84 mm.

However, without limitation to such a value, it is preferable that the radius of curvature of the sphere 71 be more than a half of the outside diameter of the catheter and not more than the outside diameter of the catheter.

Moreover, it is preferable that the opening 70 open from a position 1.0 mm to 10.0 mm apart from the center 72 (or vertex) of the sphere 71 toward the base end side.

Furthermore, it is preferable, without limitation, that the radius of curvature of the sphere 73 be larger than the radius of curvature of the sphere 71.

Needless to say, it is possible to apply the shape of the end of the top portion 34 as explained in Embodiment 5 to the catheter as explained in Embodiment 2 or any catheters of other constructions.

Embodiment 6

Embodiment 6 of this invention is hereinafter explained with reference to drawings. Concerning Embodiment 6, an explanation is given about a mode in which the end shape of the angiographic catheter as explained in Embodiment 3 is changed.

Figure 12:
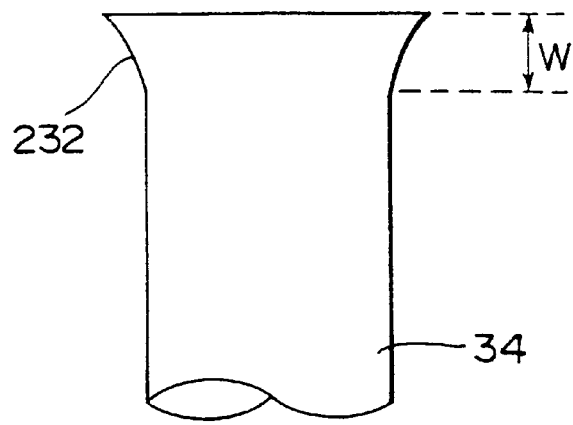
FIG. 12 is an enlarged plan view of the top portion of an angiographic catheter according to Embodiment 6 of this invention.

FIG. 12 is an enlarged plan view of the top portion of the angiographic catheter according to Embodiment 6. The same reference numerals as used in the preceding embodiments of the angiographic catheter are given to each element of the same construction in Embodiment 6. Any detailed descriptions about such elements are omitted.

The angiographic catheter shown in FIG. 12 is formed in a manner such that the end of the top portion 34 gradually becomes wider toward the outside. In other words, a tapered portion 232 which expands outward is formed at the end of the top portion 34. This tapered portion 232 has a bend shape with a 0.8 mm radius of curvature. According to Embodiment 6, the length of the tapered portion 232, that is, the distance indicated with a letter W in FIG. 12 is set as 1.5 mm. This tapered portion 232 can be formed with, for example, soft resins.

Figure 13:
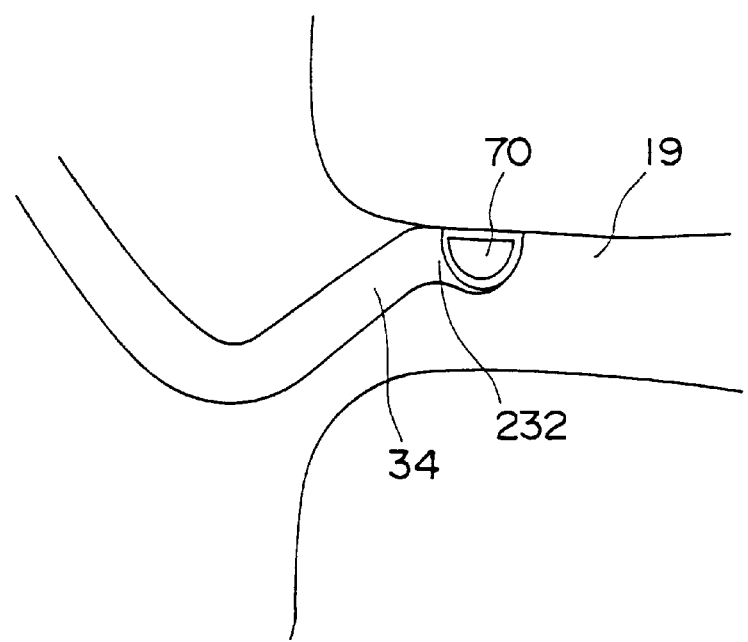
FIG. 13 is a model view of the angiographic catheter according to Embodiment 6 of this invention as used in the left coronary artery.

With the catheter in the above-described shape, for example, as shown in FIG. 13, if the catheter is inserted into the left coronary artery 19 and the end or the tapered portion 232 of the catheter touches the inner walls of blood vessels and becomes crushed, it is possible to secure the outlet for a contrast medium, thereby producing a good flowing effect of the contrast medium. It is also possible to prevent the contrast medium from being injected into the inner wall of the left coronary artery 19. Operation of the catheter becomes easier and the detainment and collection of a stent can be easily conducted.

Moreover, since the top portion of the catheter can be formed with soft materials, it is possible to prevent the inner walls of the coronary arteries or blood vessels from being injured or dissociated.

Concerning Embodiment 6, an explanation has been given about the case where the radius of curvature of the tapered portion 232 is set as 0.8 mm. However, without limitation to this value, it is preferable that the radius of curvature be set within the range of 1.0 mm to 10.0 mm.

According to Embodiment 6, the length of the tapered portion 232, that is, the distance indicated with the letter W in FIG. 12 is set as 1.2 mm. However, without limitation to this value, it is preferable that this length be set within the range of 1.0 mm to 2.0 mm.

Concerning Embodiment 6, the end shape of the left coronary artery angiographic catheter has been explained. However, without limitation to this usage, it is possible to apply the end shape as explained in Embodiment 6 to, for example, the catheter according to Embodiment 2 or any general catheters of other constructions.

Figure 14:
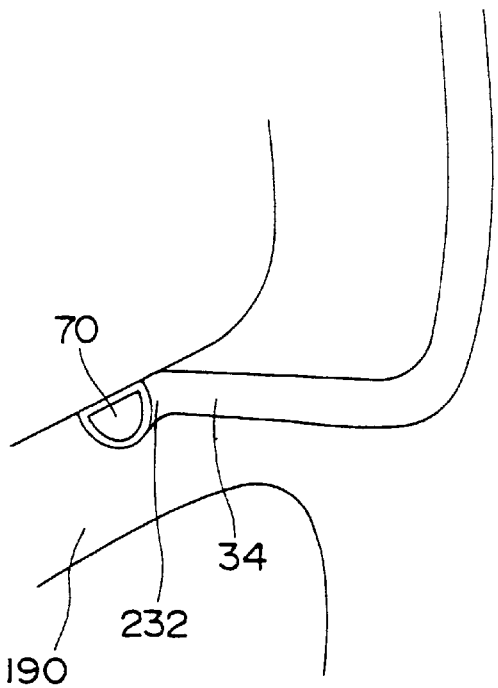
FIG. 14 is a model view of the angiographic catheter according to another embodiment of this invention as used in the right coronary artery extending downward.
Figure 15:
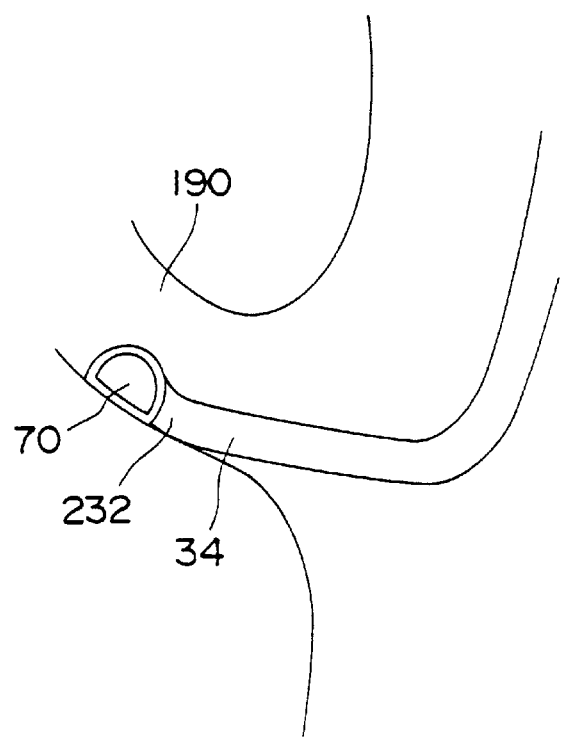
FIG. 15 is a model view of the angiographic catheter according to another embodiment of this invention as used in the right coronary artery extending upward.

For example, if the above-described end shape is applied to the end shape of a right coronary artery angiographic catheter, the same effect as described above can be obtained as shown in FIGS. 14 and 15. FIG. 14 shows an example where the catheter is used in the right coronary artery extending downward and FIG. 15 shows an example where the catheter is used in the right coronary artery extending upward.

As described above, since the catheter of this invention is provided with the aforementioned inclined portion in the top portion, it is possible to have a wide area of the end face of the catheter. Particularly, in the case of use for angiography, it is possible to prevent a contrast medium from being injected into the inner wall of the coronary artery. Accordingly, it is possible to inject the contrast medium into a desirable region with more certainty and efficiently.

Moreover, upon the operation of the left coronary artery angiographic and PTCA guiding catheter of this invention, it is possible to restrain the end of the catheter from colliding with the inlet of the left coronary artery or the inner walls of blood vessels. Accordingly, it is possible to prevent the inlet of the left coronary artery or the inner walls of the blood vessels from being injured or dissociated. As a result, the burden imposed on a patient can be reduced as much as possible.

What is claimed is:

1. A coronary artery angiographic and percutaneous transluminal coronary angioplasty guiding catheter, comprising:
    a substantially tubular distal top portion having an open distal end;
    a substantially tubular proximal main portion; and
    a substantially tubular bend portion connectively provided between said distal top portion and said proximal main portion,
    wherein at the distal end of said distal top portion an inclined portion is formed, the inclined portion being inclined such that a length of said distal top portion is shorter on an inside periphery of said bend portion than on an outside periphery of said bend portion and wherein the inclined portion comprises a closed portion being bent and sealed.

2. A coronary artery angiographic and percutaneous transluminal coronary angioplasty guiding catheter according to claim 1, wherein a radius of curvature of the outside periphery of said closed portion is within the range of 0.1 mm to 5.0 mm.

3. A coronary artery angiographic and percutaneous transluminal coronary angioplasty guiding catheter according to claim 1, wherein at the distal top portion and continuous to said closed portion a second bend portion and a third bend portion are formed in order closer to said closed portion.

4. A coronary artery angiographic and percutaneous transluminal coronary angioplasty guiding catheter according to claim 3, wherein said second bend portion is bent with the radius of curvature of the outside periphery ranging from 0.5 mm to 5.0 mm.

5. A coronary artery angiographic and percutaneous transluminal coronary angioplasty guiding catheter according to claim 3, wherein said third bend portion is bent with the radius of curvature of the outside periphery ranging from 0.5 mm to 10.0 mm.

6. An angiographic and percutaneous transluminal coronary angioplasty guiding catheter, comprising:
    a substantially tubular distal top portion having a distal end;
    a substantially tubular proximal main portion; and
    a substantially tubular bend portion connectively provided between said distal top portion and said proximal main portion,
    wherein the distal end of said distal top portion is composed of a closed sphere and an opening is formed at a position close to said sphere of said distal top portion and wherein an opening area of the opening is 1.0 to 2.0 times as large as a cross-sectional area of said distal top portion as cut in a direction perpendicular to the lengthwise direction of said distal top portion.

7. An angiographic and percutaneous transluminal coronary angioplasty guiding catheter according to claim 6, wherein the radius of curvature of said sphere exceeds one half of the outside diameter of the catheter and is not more than the outside diameter of the catheter.

8. The coronary artery angiographic and percutaneous transluminal coronary angioplasty guiding catheter as in claim 7, wherein the opening is formed from a position 1.0 mm to 10.0 mm apart from the top of said sphere in a direction away from the top of said sphere along the catheter.

9. The coronary artery angiographic and percutaneous transluminal coronary angioplasty guiding catheter as in claim 7, wherein a second sphere is formed inside the end of said distal top portion, the second sphere having a larger radius of curvature than that of said first sphere.

10. An angiographic and percutaneous transluminal coronary angioplasty guiding catheter as in claim 6, wherein the opening is formed from a position 1.0 mm to 10.0 mm apart from the top of said sphere in a direction away from the top of said sphere a the catheter.

11. An angiographic and percutaneous transluminal coronary angioplasty guiding catheter as in claim 6, wherein a second sphere is formed inside the distal end of said distal top portion, the second sphere having a larger radius of curvature than that of said first sphere.

12. A left coronary artery angiographic and percutaneous transluminal coronary angioplasty guiding catheter, comprising:

a substantially tubular distal top portion having a distal end;

a substantially tubular proximal main portion; and a substantially tubular bend portion connectively provided between said distal top portion and said proximal main portion, wherein said bend portion comprises:

a first bend portion formed closer to said proximal main portion and having a radius of curvature of the outside periphery within the range of 5.0 mm to 15.0 mm;

a second bend portion formed closer to said distal top portion and being bent in the same direction as that of the first bend portion and having a radius of curvature of the outside periphery within the range of 3.0 mm to 9.0 mm;

a first straight portion provided between the first bend portion and the second bend portion and at an angle with said proximal main portion ranging from more than 0 degrees to not more than 45 degrees; and a second straight portion provided between the second bend portion and said distal top portion and at an angle with said proximal main portion ranging from not less than 10 degrees to not more than 135 degrees, wherein said distal top portion comprises a third bend portion being bent in a direction opposite to that of said bend portion and having a radius of curvature of the outside periphery within the range of 3.0 mm to 9.0 mm, wherein said distal top portion further comprises a third straight portion at the end of the third bend portion and at an angle with said proximal main portion ranging from more than 0 degrees to not more than 85 degrees, wherein the distal end of said distal top portion is formed closer to said proximal main portion than from the second bend portion, and wherein a distance X between a line $L_1$, which is a tangent of the first bend portion and perpendicularly intersects said proximal main portion, and a line $L_2$, which passes the end of said distal top portion and perpendicularly intersects said proximal main portion, is from 34.0 mm to 55.0 mm.

13. A left coronary artery angiographic and percutaneous transluminal coronary angioplasty guiding catheter as in claim 12, wherein a ratio (X:Y) of the distance X to a distance Y between a line $L_3$, which passes a boundary point of said bend portion and said distal top portion and perpendicularly intersects said proximal main portion, and the line $L_2$ ranges from 34.0 mm:1.0 mm to 55.0 mm:5.0 mm.

14. A left coronary artery angiographic and percutaneous transluminal coronary angioplasty guiding catheter, comprising:

a substantially tubular distal top portion having a distal end;

a substantially tubular proximal main portion; and a substantially tubular bend portion connectively provided between said distal top portion and said proximal main portion, wherein said bend portion comprises:

a first bend portion formed closer to said proximal main portion and having a radius of curvature of the outside periphery within the range of 5.0 mm to 15.0 mm;

a second bend portion formed closer to said distal top portion and being bent in the same direction as that of the first bend portion and having a radius of curvature of the outside periphery within the range of 3.0 mm to 9.0 mm;

a first straight portion provided between the first bend portion and the second bend portion and at an angle with said proximal main portion ranging from more than 0 degrees to not more than 45 degrees; and a second straight portion provided between the second bend portion and said distal top portion and at an angle with said proximal main portion ranging from not less than 10 degrees to not more than 135 degrees, wherein said distal top portion comprises a third bend portion being bent in a direction opposite to that of said bend portion and having a radius of curvature of the outside periphery within the range of 3.0 mm to 9.0 mm, wherein the distal end of said distal top portion is formed closer to said proximal main portion than from the second bend portion, and wherein a distance X between a line $L_1$, which is a tangent of the first bend portion and perpendicularly intersects said proximal main portion, and a line $L_2$, which passes the end of said distal top portion and perpendicularly intersects said proximal main portion, is from 34.0 mm to 55.0 mm.

15. A left coronary artery angiographic and percutaneous transluminal coronary angioplasty guiding catheter as in claim 14, wherein a ratio (X:Y) of the distance X to a distance Y between a line $L_3$, which passes a boundary point of said bend portion and said distal top portion and perpendicularly intersects said proximal main portion, and the line $L_2$ ranges from 34.0 mm:1.0 mm to 55.0 mm:5.0 mm.

* * * * *